(12) United States Patent
Nguyen et al.

(10) Patent No.: US 8,563,014 B2
(45) Date of Patent: Oct. 22, 2013

(54) MODAFINIL ORAL LYOPHILIZATE

(75) Inventors: Thanh-Tam Nguyen, Limeil-Brevannes (FR); Joëlle Leyder, Creteil (FR)

(73) Assignee: Teva Sante, Cedex (FR)

( * ) Notice: Subject to any disclaimer, the term of this patent is extended or adjusted under 35 U.S.C. 154(b) by 0 days.

(21) Appl. No.: 13/094,578

(22) Filed: Apr. 26, 2011

(65) Prior Publication Data

US 2011/0229578 A1   Sep. 22, 2011

Related U.S. Application Data

(63) Continuation of application No. 11/191,559, filed on Jul. 28, 2005, now abandoned.

(60) Provisional application No. 60/598,553, filed on Aug. 4, 2004.

(30) Foreign Application Priority Data

Jul. 29, 2004   (EP) .................................... 04291946

(51) Int. Cl.
| | | |
|---|---|---|
| *A61K 9/50* | (2006.01) | |
| *A61K 9/14* | (2006.01) | |
| *A61K 31/165* | (2006.01) | |
| *A61P 25/00* | (2006.01) | |
| *A61P 3/04* | (2006.01) | |
| *A61P 25/20* | (2006.01) | |

(52) U.S. Cl.
USPC ............................ 424/400; 424/490; 514/618

(58) Field of Classification Search
USPC ..................... 424/490, 400; 514/618
See application file for complete search history.

(56) References Cited

U.S. PATENT DOCUMENTS

| | | | | |
|---|---|---|---|---|
| 3,641,236 | A | * | 2/1972 | Coppen et al. ................. 424/465 |
| 3,767,807 | A | | 10/1973 | Blonde et al. |
| 4,177,290 | A | | 12/1979 | Lafon |
| 4,927,855 | A | | 5/1990 | Lafon |
| 5,180,745 | A | | 1/1993 | Lafon |
| 5,843,347 | A | * | 12/1998 | Nguyen et al. ..................... 264/9 |
| RE37,516 | E | | 1/2002 | Grebow et al. |
| 6,346,548 | B1 | | 2/2002 | Miller et al. |
| 6,455,588 | B1 | | 9/2002 | Scammell et al. |
| 7,141,555 | B2 | * | 11/2006 | Jacobs et al. .................... 514/58 |
| 7,749,540 | B2 | | 7/2010 | Jacobs et al. |

FOREIGN PATENT DOCUMENTS

| | | |
|---|---|---|
| EP | 0547952 | 6/1993 |
| EP | 0594507 | 4/1994 |
| EP | 1621186 | 1/2006 |
| FR | 2385693 | 10/1978 |
| WO | WO02/56915 | 7/2002 |
| WO | WO2004/006905 | 1/2004 |
| WO | WO2004/024133 | 3/2004 |
| WO | WO2004/024134 | 3/2004 |

OTHER PUBLICATIONS

U.S. Appl. No. 60/204,789, filed May 16, 2000, Chatterjee et al.
Bastuji et al., "Successful Treatment of Idiopathic Hypersomnia and Narcolepsy with Modafinil", Prog., Neuro-Psych. Biol. Psych., 1988, pp. 695-700.
Duteil et al., "Central α1-Adrenergic Stimulation in Relation to the Behaviour Stimulating Effect of Modafinil; Studies with Experimental Animals", Eur. J. Pharmacol., 1990, 180, pp. 49-58.
European Search Report, dated Mar. 5, 2005.

* cited by examiner

*Primary Examiner* — Fereydoun G Sajjadi
*Assistant Examiner* — Courtney Brown (57) ABSTRACT

The invention concerns an oral lyophilizate comprising modafinil particles having a median diameter of about 10 to about 1000 μm in association with an appropriate amount of at least one excipient selected from the group consisting of fatty acid esters of glycerol, cyclic oligosaccharides, sweeteners or mixtures thereof.

14 Claims, 3 Drawing Sheets

MODAFINIL ORAL LYOPHILIZATE

CROSS REFERENCE TO RELATED APPLICATIONS

This application is a Continuation application of U.S. patent application Ser. No. 11/191,559, filed Jul. 28, 2005, which claims priority to U.S. Provisional Application Ser. No. 60/598,553 filed Aug. 4, 2004. A right to priority is also claimed under 35 U.S.C. §119 of European Patent Application No. 04291946.4, filed Jul. 29, 2004. The disclosures of these priority applications are incorporated herein by reference in their entireties for all purposes.

FIELD OF THE INVENTION

The present invention is related to oral lyophilizates of modafinil and a process of preparation thereof. The present invention relates to palatable lyophylizate that include modafinil and at least one or more diluents, binders and taste-masking, sweeteners and flavors. The present invention further relates to processes for preparing a solid form of modafinil by mixing and lyophilizing modafinil and excipients.

BACKGROUND OF THE INVENTION

Modafinil, $C_{15}H_{15}NO_2S$ of formula (I), is also known as 2-(benzhydrylsulfinyl)acetamide, or 2-[(diphenylmethyl)sulfinyl]acetamide:

Formule (I)

Modafinil is a synthetic acetamide derivative described in the French patent no. 78 05510 and in U.S. Pat. No. 4,177,290 ('290) as presenting a "neuropsychopharmacological spectrum characterized by the presence of excitation with hyperactivity and of hypermotility; and by the absence of stereotypy (except in high doses) and of potentialization of the effects of apomorphine and amphetamine". A single administration of modafinil results in increased locomotor activity in mice and increased nocturnal activity in monkeys. Duteil et al., *Eur. J. Pharmacol.*, 1990, 180, 49. Modafinil has been successfully tested in humans for treatment of idiopathic hypersomnia and narcolepsy, Bastuji et al., *Prog. Neuro-Psych. Biol. Psych.*, 1988, 12, 695.

Modafinil has also been described as an agent with activity in the central nervous system. U.S. Pat. No. 5,180,745 discloses the use of modafinil for providing a neuroprotective effect in humans, and in particular for the treatment of Parkinson's disease. The levorotatory form of modafinil, i.e., (−) or R-benzhydrylsulfinyl-acetamide, may have potential benefit for treatment of depression, hypersomnia and Alzheimer's disease (U.S. Pat. No. 4,927,855). EP-A-547952 discloses the use of modafinil as an anti-ischemic agent. EP-A-594507 discloses the use of modafinil to treat urinary incontinence. In addition, modafinil may be useful in the treatment of eating disorders, or to promote weight gain or stimulate appetite in human or animals (U.S. Ser. No. 09/640,824, incorporate herein by reference) or in the treatment of attention deficit disorders (ADHD), or fatigue, especially fatigue associated with multiple sclerosis (U.S. Pat. No. 6,346,548 incorporated herein by reference).

Preparations of modafinil having a defined solid particle size are described in US RE 37516 and preparations of a levorotatory isomer of modafinil are described in U.S. Pat. No. 4,927,855, RE 37516 and U.S. Pat. No. 4,927,855 being incorporated herein by reference. Heterocyclic derivatives of modafinil are disclosed in the application U.S. 60/204,789.

Modafinil was launched in 1994 as Modiodal® for the treatment of idiopathic hypersomnia and narcolepsy in France. In the United States, it was launched as Provigil® for the treatment of excessive daytime sleepiness (EDS) associated with narcolepsy (1999) and more recently has been approved for EDS associated with obstructive sleep apnoea/hypopnoea syndrome and moderate-to-severe chronic shift work sleep disorder (SWSD). Modafinil is marketed as fairly large tablets containing 100 mg or 200 mg of the drug per tablet and several excipients such as a diluent, a disintegrant, a binder and a lubricant.

Solid dosage forms such as tablets or capsules and improved manufacturing processes have recently been disclosed in WO 2004/024133. Novel compressed tablets containing 100 mg to 200 mg modafinil in a 250 or 500 mg tablets or up to 90% modafinil in 225 mg tablets exhibit similar specifications as the marketed ones regarding, in particular, size and shape.

Higher unit doses may be used to simplify the dose schedule to one daily administration with the same therapeutic efficacy.

WO 2004/024134 discloses modafinil tablets of reduced overall unit size with an increase in weight percent of modafinil and a reduced weight percent of other ingredients for treating ADHD, a chronic neuropsychiatric disorder in children or adults patients, administered at a single dose of about 250 to 450 mg of modafinil per tablet within a 24-hour period.

Nevertheless, although these modafinil tablets offer potential advantages regarding dose schedule by reducing the total number of doses of modafinil required per day by a patient, and a decreased size/volume, patients may remain noncompliant to their treatment, particularly when high dosage units are indicated for the treatment of disease or disorders.

This applies in particular to patients experiencing difficulties in swallowing, or being unable to swallow tablets, or disliking swallowing tablets, or who may require a liquid to assist swallowing of tablets, such as for example pediatric or geriatric patients.

Administered via the oral route, significant plasma concentrations of modafinil have to be maintained in a therapeutic range for a sufficient period of time to continue to promote wakefulness in patients suffering of EDS associated for example with narcolepsy. Due to the short half-life of the compound, multiple dosing or high dosage forms may be necessary to maintain the patient in a wakeful state.

Thus, there is further a need for such improved oral delivery of modafinil which maintains blood concentrations at a suitable level and provides minimal variation in blood levels, to achieve a longer duration of action.

Liquid oral dosage forms of modafinil comprising a complex of a modafinil compound and a cyclodextrin are disclosed in the patent application WO 02/056915. The cyclodextrin increases bioavailability of the modafinil compound by enhancing the solubility of the modafinil compound in water.

However, dosing of active ingredients in liquid form is a random process even when using a dose spoon. Also, liquid dosage forms generally contain saccharose or sodium which are not suitable for patients subjected to a restrictive diet.

Oral lyophilizates, also called oral Lyoc™ are porous, crumbly solid preparations for oral administration disclosed for example in U.S. Pat. No. 3,767,807. They are prepared by lyophilization of an aqueous solution, of a suspension or of an emulsion of an active ingredient and excipients. Oral lyophilizates prepared from emulsions or suspensions of active ingredients are not subjected to compression and the integrity of a substance, particularly the initial particle-size distribution, may thus be preserved.

Lyophilizate manufacturing process proceeds by freezing an appropriate form of the active ingredients at very low temperature (generally at −20° C. to −50° C.). Subsequent lyophilization under reduced pressure has the advantage of protecting the active ingredients from degradation due to heat and water and to improve storage stability. As a result, oral lyophilizates exhibit an extremely low level of degradation impurities as well as an enhanced chemical and physical stability. The use of additives and preserving agents is thus generally unnecessary.

Lyophilization further increases the hydrophilic character of the particles. The porous structure of lyophilizates reduces particle agglomeration in water. Hence, the integrity of the original particle size is preserved and electrostatic phenomena are eliminated. Thus, the amount of excipients such as disintegrants in the formulation may be reduced.

This dosage form further affords many therapeutic advantages such as a better digestive tolerance, and a fast onset of action. Oral lyophilizate are also easily administered. They may be ingested without water by placing the Lyoc™ under the tongue, crunching between the teeth or allowing it to disintegrate in the mouth facilitating compliance as well as ambulatory treatment.

Lyophilized microbeads of modafinil are disclosed in U.S. Pat. No. 5,843,347. These beads have a diameter of about 1 mm and are prepared with modafinil particles of 2-5 µm in diameter. Hydroxypropyl- -cyclodextrin is included as an inert diluent and to improve the cohesion of the microbeads.

Due to their small size (diameter 1 mm), the microbeads are intended to be swallowed immediately without prior crunching or disintegration in the mouth, rendering the taste-masking of the modafinil bitter taste not an issue for such composition.

In addition, due to the small size of the microbeads, their modafinil dosage strength is very limited. This dosage form is thus not suitable for a convenient administration of high strength modafinil dosages.

There is thus a need for an oral dosage form of modafinil, in particular aimed to deliver high dosage forms, which is easy to swallow and has an acceptable taste. It is further desirable to provide such a dosage form which further allows controlled release.

SUMMARY OF THE INVENTION

The present invention is directed to oral lyophilizates comprising a modafinil compound. Preferably, the oral lyophilizate comprises modafinil compound particles having a median particle size of about 10 to about 1000 µm.

The present invention is also directed to an oral lyophilizate of modafinil compound wherein the modafinil compound is taste-masked and the composition is palatable. In preferred embodiment, the oral lyophilizate comprises a modafinil compound having median particle size of 10 to 200 µm in association with a diluent and an efficient amount of at least one excipient selected from the group consisting of cyclic oligosaccharides, fatty acid esters of glycerol, sweeteners, flavors, bitter blockers or mixture thereof. In another preferred embodiment, the oral lyophilizate comprises a modafinil compound having median particle size of 100 to about 1000 µm, notably 200 to about 1000 µm in association with a diluent and with an efficient amount of at least one excipient selected from the group consisting of sweeteners, flavors, bitter blockers or mixture thereof.

The present invention is also directed to an oral lyophilizate of modafinil compound easy to swallow with a median maximal diameter of 10 to 20 mm preferably 14 to 16 mm and a thickness of 2 to 10 mm, preferably 3 to 7 mm.

The present invention is also directed to an oral lyophilizate of modafinil compound which allows the precise administration of a unit dose of modafinil. Preferably, the present invention also provides a formulation for oral administration of about 50 to about 850 mg, and in particular about 250 to about 850 mg, of a modafinil compound per unit dose.

The present invention is also directed to an oral lyophylizate of a modafinil compound with immediate release properties equivalent to marketed tablets. Preferably the oral lyophylizate comprise a modafinil compound having median particle size in the 10 to 315 µm range, more preferably in the 20-40 µm range.

The present invention is also directed to sustained-release oral lyophilizate of a modafinil compound. In certain preferred embodiment the sustained-release composition comprises a modafinil compound having median particle size in the 315 to about 1000 µm range. In another preferred embodiment the sustained-release composition comprises a modafinil compound having median particle size in the about 10 to about 1000 µm range with an efficient amount of at least one excipient selected from fatty acid esters of glycerol.

The present invention is also directed to a method for the manufacture of an oral lyophilizate of a modafinil compound. In particular, the process involves:
(i) the preparation of an aqueous suspension comprising a modafinil compound particles and an excipient selected from the group consisting of cyclic oligosaccharides, fatty acid esters of glycerol, sweeteners or a mixture thereof and optionally one or more excipients;
followed by:
(ii) the lyophilization of the obtained suspension.

The present invention is also directed to methods of treating a disease or disorder in a subject which comprises administering to the subject a therapeutically effective amount of the oral lyophylizate of the present invention.

DETAILED DESCRIPTION OF THE INVENTION

The present invention is directed to an oral lyophilizate comprising a modafinil compound which is palatable and allows the precise administration of a unit dose of a modafinil compound that may exhibit either immediate-release or sustained-release properties.

As used above, and throughout the description of the invention, the following terms, unless otherwise indicated, should be understood to have the meaning given below.

As used herein, the term "oral lyophilizate" refers to an oral formulation obtained by lyophilization of an aqueous suspension or solution comprising the active ingredient in combination with pharmaceutically acceptable excipients, without any further step of compression.

As used herein, the term "about" refers to a range of values ±10% of the specified value. For example, "about 20" includes ±10% of 20, or from 18 to 22.

As used herein, "modafinil" or "modafinil compound" refers to modafinil, its racemic mixtures, its individual isomers (for example, the (−) isomer or the "R" isomer of modafinil, polymorphic forms, analogs, derivatives, cogeners, pharmaceutically acceptable salts forms, and prodrug thereof.

"Modafinil derivatives" refer in particular to compounds acid addition salts, such as a metabolic acid of modafinil, benzhydrylsulfinylacetic acids, and its sulfone forms and hydroxylated forms.

"Prodrugs" are known in the art as compounds that are converted into the active ingredient, i.e. modafinil, within the body of a subject or patient. More specifically, as used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.), modafinil may be delivered in prodrug form. Conventional procedures for the selection and preparation of suitable prodrug derivatives are described, for example, in Prodrugs, Sloane, K. B., Ed.; Marcel Dekker: New York, 1992, which is incorporated herein by reference in its entirety.

As used herein, "unit dose" means a single dose which is capable of being administered to a subject, and which can be readily handled and packaged, remaining as a physically and chemically stable unit dose comprising either modafinil or a modafinil derivative, or a pharmaceutically acceptable composition comprising modafinil or a modafinil derivative.

As used herein, the term "subject" refers to a warm blooded animal such as a mammal, preferably a human or a human child, which is afflicted with, or has the potential to be afflicted with one or more diseases and conditions described herein.

As used herein, the term "therapeutically effective amount" refers to an amount which is effective in reducing, eliminating, preventing or controlling the symptoms of the herein-described diseases and conditions. The term "controlling" is intended to refer to all processes wherein there may be a slowing, interrupting, arresting, or stopping the progression of the diseases and conditions described herein, but does not necessarily indicate a total elimination of all disease and condition symptoms, and is intended to include prophylactic treatment.

As used herein, the term "pharmaceutically acceptable" refer to those compounds, materials, compositions, and/or dosage forms which are, within the scope of a sound medical judgment, suitable for contact with tissues of human beings and animals without excessive toxicity, irritation, illogic response or other problems, complications with a reasonable benefit/risk ratio.

"Excipients" refers to substances that are used in the formulation of pharmaceutical compositions and, by themselves, generally have little or no therapeutic value. Typical excipients include diluents, disintegrants, lubricants, binders, surfactants, sweeteners, flavors, taste enhancers, anti-oxidants, antibacterial agents and substances commonly used in pharmaceutical compositions.

The term "fatty acid esters of glycerol" also called "fatty acid glycerides" refers to mono-, di- or triesters of fatty acids with glycerol.

As used herein, "fatty acids" refers to compounds of formula Alk-COOH, wherein "Alk" represents an aliphatic hydrocarbon group which may be straight or branched, saturated or unsaturated, having about 6 to about 48 carbon atoms. Preferred alkyl groups have about 12 to about 24 carbon atoms. "Lower alkyl" means about 1 to about 4 carbon atoms in the chain which may be straight or branched. Examples of fatty acids include notably caprylic, capric, lauric, myristic, palmitic, stearic, linoleic and oleic acids.

The term "cyclic oligosaccharides" refers to cyclic carbohydrates of from 3 to 6 units of simple sugars (monosaccharides) and their derivatives.

The term "cyclodextrin" refers to the natural cyclodextrins, α-cyclodextrin, β-cyclodextrin and γ-cyclodextrin and their respective derivatives. Cyclodextrin consists of glucose units linked in a ring configuration, and more specifically they are cyclic oligosaccharides composed of α-(1,4)-linked D-glucopyranosyl units. Preferably, cyclodextrin is a β-cyclodextrin which includes β-cyclodextrin and its derivatives. Derivatives are typically prepared by modifying the hydroxyl group located on the exterior or hydrophilic side of the cyclodextrin. Examples of cyclodextrin derivatives include notably hydroxypropyl-β-cyclodextrin and β-cyclodextrinsulfobutylether. A mixture of modafinil with cyclodextrin may refer to a complex of modafinil compound and a cyclodextrin, or to a composition comprising a modafinil compound and a cyclodextrin.

As used herein, "particle" refers to an aggregated physical unit of matter, such as a piece or a grain.

As used herein, the term "median" when used in reference to the diameter of modafinil particles indicates that about 50% of all measurable particles measured have a particle diameter less than the defined median particle diameter value, and that about 50% of all measurable particles measured have a particle diameter greater than the defined median particle diameter value.

As used herein, the terms "particle diameter" refers to a volumetric measurement based on the presumed spherical shape of particles.

As used herein, the term "monodisperse" refers to particles having a uniform size. More specifically, it refers to a population of particles showing a narrow and homogenous particle size distribution. As an example, 20-40 µm refers to a monodisperse particle size distribution.

"Sustained-release" refers to dosage forms with delayed, controlled, extended or polymodal, for example bimodal release properties. More specifically, it is referred to a dosage form wherein less than about 75% by weight of the active substance are dissolved in 0.1M HCl at 37° C. within 30 minutes.

"Immediate release" refers to dosage forms wherein more than about 75% of the active substance are dissolved in 0.1M HCl at 37° C. within 30 minutes.

"Discrete lots" refers to monodisperse lots containing particles of modafinil of pre-determined or bounded particle size.

Accordingly, there is provided an oral lyophilizate comprising modafinil and one or more excipients to allow for taste-masking as needed including taste-masking agent, sweeteners, flavors agents, taste enhancers and bitter blockers to render the compositions palatable.

The present invention also provides a modafinil lyophilizate unit dose easy to swallow, which are particularly suitable for geriatric and pediatric patients. Therefore, the maximum diameter of the oral lyophilizate unit dose is in the 10 to 20 mm range, preferably the maximum diameter is from 14 mm to 16 mm and the thickness of the oral lyophilizate unit dose ranges from 2 to 10 mm, notably 2 to 7 mm, preferably 3 to 7 mm.

Generally, the weight of the lyophilizate unit dose will not exceed 1000 mg for 850 mg modafinil dose.

Preferred features of the present invention are described in the present application purely by way of examples, with reference to the accompanying figures.

1. Modafinil

In a first embodiment, the present invention is directed to an oral lyophilizate comprising modafinil particles having a median diameter of about 10 to about 1000 microns in association with an appropriate amount of at least one excipient selected from the group consisting of cyclic oligosaccharides, fatty acid esters of glycerol, sweeteners, flavors or mixture thereof.

During the manufacturing process of oral lyophilizates, particles are not compressed. Consequently, the particles size is preserved during the whole process and particles do not agglomerate. Hence, the size of the modafinil particles ingested when administering an oral lyophilizate to a subject is similar to the initial particle size used for the manufacture of the compositions.

Several properties of the dosage form depend upon the particle size. Notably, the bitter taste may be more or less intense. Modafinil in granular form or in solution has a bitter, metallic taste making the compound less desirable for oral administration. It has been found that this property is linked to particles with a median diameter below to 200 μm while modafinil particles with a median diameter greater than 200 μm do not exhibit a bitter taste.

The relative percentage of taste-masking agents including cyclodextrin, fatty esters of glycerol and/or also sweeteners, flavors and/or taste enhancers, bitter blockers will thus depend on the median diameter of modafinil compound particles.

The dissolution rate of modafinil depends also on particle size, i.e. the smaller the particles, the higher the dissolution rate and thus the modafinil release rate. In order to precisely control the release rate, modafinil particles with specific median diameter and a monodisperse particle size distribution or mixture thereof are thus preferred.

The preparation of discrete particle size lots of modafinil having a bounded defined particle diameter range has been described in WO 04/006905, which is incorporated herein by reference. Other methods, such as milling, micronization, separation by weight, separation by density, etc. . . . may be used to prepare pre-determined particle size lots. Different lots with bounded particle size may also be combined as to prepare lyophilizate of modafinil combining immediate release and sustained-release properties.

In addition, the relative proportion of the excipients may be chosen such as to obtain a predetermined modafinil release rate.

The particle size further may have an impact regarding the mechanical properties of the oral lyophilizate, such as the disintegration time and the hardness.

Accordingly, there is provided an oral lyophilizate that presents a disintegration time of less than 3 minutes, as measured either according to the USP method (<701> USP 26) or using a specific method as recommended for oral lyophilizate by the European pharmacopoeia, and preferably 2 to 60 seconds.

According to another aspect, there is provided an oral lyophilizate that has a hardness of 5 N to 60 N, preferably 7 N to 30 N as measured with the Schleuniger® apparatus (Schleuniger, Switzerland).

According to an another aspect, there is provided an oral lyophilizate with a percent dissolution at 30 minutes between 25% and 100% by weight of the active substance when using the referenced dissolution kinetic assay. In a preferred aspect, the immediate-release lyophilizates exhibit a percent dissolution at 30 minutes higher than 75%, and more preferably about 85% to 100% by weight of the active substance are dissolved in 30 minutes in the dissolution test. In another preferred aspect, the lyophilizates exhibit a percent dissolution at 30 minutes within 10% and 75% to achieve sustained-release properties, preferably 25% to 60% by weight of the active substance.

Generally, modafinil particles with a median particle size of about 10 to about 1000 μm have been found to be appropriate for the preparation of oral lyophilizates.

Indeed, the use of modafinil particles with a median diameter of less than about 10 μm (micronized particles) for the manufacture oral lyophylizate would require a very large amount of taste-masking agent and would thus lead to a bulky oral lyophilizate. Also, the rate of dissolution of modafinil particles with a median diameter greater than about 1000 μm tends to be slower and may delay the onset of action.

In a preferred embodiment of the present invention, modafinil particles with a median diameter between about 10 and 315 μm, preferably between 10 and 200 μm and more preferably between 20 and 40 μm are used. In another preferred embodiment, modafinil particles having a median diameter between 315 μm and about 1000 μm are used to prepare the oral lyophilizate with sustained-release properties.

In a further preferred embodiment, the oral lyophilizates of modafinil include at least one pharmaceutical unit dose. The present invention provides oral lyophilizate containing between about 50 mg and about 850 mg of modafinil.

In a preferred embodiment, the lyophilizate unit dose can contain 50 to 260 mg by weight of modafinil, including more preferably about 85 mg to about 255 mg of modafinil by weight with respect to the unit dose weight. As an example, the lyophilizate unit dose may contain 85, 170 or 255 mg of modafinil by weight with respect to the unit dose weight.

In another preferred embodiment, the proportion of modafinil in the unit dose can be higher than that of conventional 100 mg and 200 mg of modafinil tablets, containing preferably about 200 mg to about 850 mg, more preferably about 250 mg to 450 mg by weight of modafinil with respect to the unit dose weight. As an example, the lyophilizate unit dose may contain 255, 340 or 425 mg of modafinil by weight with respect to the unit dose weight.

In another embodiment, the total amount of modafinil per unit dose can be from about 10% to about 90% with respect to the unit dose weight. Preferably, the total amount of modafinil present in a unit dose can be about 40% to about 85%, more preferably 60% to 85% by weight.

In preferred embodiments, the total weight percent in ingredients (other than modafinil) can be advantageously reduced to facilitate the manufacturing of small (size/volume) oral lyophilizate unit dose while supplying high amount of the active principle to a subject.

2. Excipients

The excipients are selected to ensure the delivery of a convenient amount of modafinil in a unit dosage lyophilizate form according to a controlled process, to facilitate the oral administration of modafinil and to optimize the reliability of the manufacturing process. All excipients are preferably inert and organoleptically acceptable, and compatible with modafinil. Preferably, the excipients meet the standards of National formulary (NF) or the United States Pharmacopoeia (USP) or the European Pharmacopoeia (EP). The excipients include:

- taste-masking agents, sweeteners and flavors added in an appropriate amount to taste-mask the modafinil bitter taste and render the modafinil oral lyophilizate palatable. The amount of those excipients depends on the amount of modafinil and its particle size and on the taste-masking capacity of the excipients,
- water soluble or water dispersible components which acts as a physiologically inert diluent, to improve the powder flow and mixture as well as the compacibility of the active principle ingredient and the other excipients.

and, optionally:
- a binder, to improve mechanical resistance of the finished product,
- a disintegrant, a surfactant, a suspension agent,
- additional taste enhancers and/or bitter blockers.

2.a) Taste-Masking Agents

It has been discovered that two kinds of taste-masking agents may be advantageously used for taste-masking modafinil bitter taste: cyclic oligosaccharides and fatty acid esters of glycerol and mixture thereof. One or more sweeteners may also be used as a taste-masking excipient when a weaker taste-masking effect is required. Further, additional agents such as sweeteners, flavors, and/or bitter blockers may also be present.

Fatty Acid Esters of Glycerol

It has been discovered that fatty acid esters of glycerol could be useful excipients:
i) for efficiently mask the bitter taste of modafinil,
ii) to manufacture oral lyophilizate of modafinil with sustained-released properties.

According to a preferred embodiment, the fatty esters of glycerol are present in the oral lyophilizate in form of a coating of the modafinil particles or binding by granulation of modafinil particles.

This coating is a convenient way of introducing the excipient and enhances the taste-masking properties. This embodiment is further interesting since it allows sustaining modafinil release.

The taste-masking capability of fatty esters of glycerol per weight of active principle is very efficient.

Less than about 10%, notably about 1% to about 5% by weight of fatty acid ester of glycerol with respect to the weight of modafinil is generally sufficient to achieve modafinil palatable oral lyophilizates with immediate release properties, in case of modafinil particles with a median particle size of 10 to 200 μm are used.

In another embodiment, the addition of fatty esters of glycerol in higher amount affects the release kinetics of modafinil particles, since the dissolution of the modafinil cannot proceed before the coating is eliminated. Accordingly, the proper choice of the thickness and nature of the coating allows a release control of the modafinil of the oral lyophilizates. For this purpose, an amount of more than about 10%, notably from about 10% to about 50% by weight of fatty esters of glycerol with respect to the weight of modafinil is appropriate.

Accordingly, the oral lyophilizate comprises fatty acid glycerol esters in an amount of up to about 50%, preferably of up to about 20% and most preferably of up to about 10% by weight of modafinil.

Therefore, modafinil particles coated with a fatty acid glycerol ester may be used to keep the overall quantity of excipient low.

In a preferred embodiment, glycerol esters are saturated or unsaturated fatty acids glycerides containing up to 48 carbon atoms, preferably from 6 to 24 carbon atoms.

Preferably, glycerol ester is selected from the group consisting of mono-, di- and/or triglycerides of fatty acids and mixtures thereof. Such fatty acids may be selected from the group consisting of dibehenic acid, palmitostearic acid, stearic acid, oleic acid, linoleic acid, caprylic acid, capric acid or mixtures thereof. Mention may be made notably of glyceryl dibehenate, glyceryl palmitostearate, glyceryl monostearate, glyceryl monooleate or caprylocapric glycerides such as glyceryl tricaprilocaprate.

The mono-, di- and/or triglycerides of palmitostearic acid or a mixture thereof are particularly preferred. Most preferably, the fatty acid glycerol ester is a mixture of mono-, di- and/or triglycerides of palmitostearic acid wherein the diester fraction is predominant, which means that the diglyceride of palmitostearic acid represents the main fraction by weight of the total weight of the mixture of mono-, di- and/or triglycerides of palmitostearic acid. In particular, the diglyceride of palmitostearic acid may represent more than 33.33%, notably more than 50% by weight of the total weight of the mixture of mono-, di- and/or triglycerides of palmitostearic acid.

Fatty acid glycerol esters may be selected in particular from:
- glyceryl palmitostearate such as sold under the trademark Precirol® ATO5;
- glyceryl tribehenate such as sold under the trademark Compritol® 888;
- glyceryl monostearate such as sold under the trademark Monomuls® 90/25;
- glyceryl monooleate such as sold under the trademark Myverol® 18/99;
- glyceryl tricaprylate/caprate such as sold under the trademark Labrafac® lipophile;
- lauroyl macrogole glycerides such as sold under the trademark Gelucire® (44/14 Gattefosse);
- stearoyl macrogole glycerides such as sold under the trademark Gelucire® (50/13 Gattefosse);
- polyglyceryloleate;
- caprylo caproyl macrogole glycerides such as sold under the trademark Labrasol®;
- polyglyceryl isostearate;
- polyglyceryl oleoleate;
- mono and triglycerides such as sold under the trademark Capmul® (Abitex);
- polyglycerol esters such as sold under the trademark Caprol® (Abitex).

Cyclic Oligosaccharides

According to a preferred embodiment, the cyclic oligosaccharides are natural cyclodextrins or their derivatives. Natural cyclodextrins include α-, β- and γ-cyclodextrins, β-cyclodextrins being particularly preferred.

Cyclodextrins may be used to mask the bitter taste of modafinil.

In addition, cyclodextrins increase the solubilization of modafinil and thus contribute to a quicker dissolution and an increase bioavailability of modafinil. Therefore, a proportion of cyclodextrin in the oral lyophilizate will thus act towards speeding up the modafinil release.

Cyclodextrins form a complex with the drugs. The degree of complexation can vary depending on the size of the drug, the degree of inclusion, the type of cyclodextrin and the concentration of the cyclodextrin. The cyclodextrin:modafinil complex has a molar ratio of 1:1. A cyclodextrin:modafinil molar ratio superior to 0.8:1 was required to achieve the required solubility and taste-masking properties of cyclodextrin when preparing a modafinil solution according to WO 02/056915. The present invention contemplates a molar ratio of cyclodextrin to a modafinil compound to be up to about 0.7:1. The inventors have discovered that the required taste-masking properties of the modafinil oral lyophilizate could be obtained with a cyclodextrin:modafinil molar ratio below than 0.7:1 when the addition of cyclodextrin into the oral lyophilizate is combined either with appropriate amounts of sweeteners and/or with fatty esters of glycerol. Consequently, the quantity of modafinil per unit dose weight could be increased while the size (diameter and thickness) of the oral lyophilizate is decreased.

According to a preferred embodiment, the oral lyophilizate comprises cyclic oligosaccharides up to about 70% by weight with respect to the modafinil weight, more preferably up to about 30% by weight of cyclic oligosaccharides with respect to the weight of modafinil.

Preferably, cyclodextrin is added when strong taste-masking is required. This is the case in particular for modafinil with a mean particle size of 10-200 µm, notably of 10-100 µm. Cyclodextrin derivatives are preferably β-cyclodextrin derivatives and include alkylated cyclodextrins, preferably methyl, dimethyl, trimethyl and ethyl cyclodextrins; hydroxyalkylated cyclodextrins, including hydroxyethyl nand hydroxypropyl-cyclodextrin; ethylcarboxymethylcyclo-dextrins; sulfates, sulfonates and sulfoalkylcyclodextrins, preferably cyclodextrin sulphate, cyclo-dextrinsulfonate and cyclodextrinsulfobutylether; as well as polymeric cyclo-dextrins. Other cyclodextrin derivatives can be made by substitution of the hydroxy group with saccharides, such as glucosyl and maltosyl cyclodextrin.

Preferred cyclodextrins include the naturally occurring cyclodextrins, methyl-β-cyclodextrins, dimethyl-β-cyclodextrins, trimethyl-β-cyclodextrins, 2-hydroxy-methyl-β-cyclodextrins, hydroxyethyl-β-cyclodextrins, 2-hydroxypropyl-β-cyclo-dextrins, β-cyclodextrinsulfate, β-cyclodextrinsulfonate, and β-cyclodextrin-sulfobutylether. Most of these are commercially available.

More preferred cyclodextrins include β-cyclodextrins, hydroxypropyl-β-cyclo-dextrins and β-cyclodextrinsulfobutylether.

Sweeteners

Oral lyophilizate according to the invention may not include any glyceryl ester or cyclic oligosaccharide.

One or more sweeteners may thus be used as a sole taste-masking excipient, i.e. without glyceryl ester or cyclic oligosaccharide, when a weak taste-masking effect is needed. This is the case in particular for modafinil with a median particle size of 100 µm-1000 µm, particularly of 100 µm-500 µm, and more particularly of 100 µm-315 µm.

Sweeteners are preferably selected from the group consisting of aspartam, saccharine, sodium saccharinate, potassium acesulfam, maltitol, isomaltidex, sodium cyclamate, sucralose and mixtures thereof, sucralose, aspartam and acesulfam being particularly preferred.

One or more sweeteners may also be used as a sole taste-masking agent with modafinil having a median diameter of 10 µm to 100 µm, notably of 20 µm to 40 µm. However, in that case, a large amount of sweetener may be needed for efficiently taste-masking the bitterness of modafinil so that the size of the resulting oral lyophilizate may be too big and hence not acceptable. This issue may be solved by using natural or synthetic sweeteners having an intense sweetening power. Such efficient sweeteners may be selected from the group consisting of sweeteners which are more than 10 times sweeter than saccharose, preferably more than 100 times, notably 100 to 1000 times, such as cyclamate, saccharine or salts thereof such as sodium saccharinate, aspartam, alitame and sucralose, sucralose being particularly preferred.

As an example, a taste-masked oral lyophilizate having an acceptable size may be obtained from modafinil particles having a median diameter of 20-40 µm in association with an appropriate amount of sucralose as a sole taste-masking agent (without any glyceryl ester or cyclic oligosaccharide).

Preferably, the oral lyophilizate of modafinil includes further one or more sweeteners, flavors, bitter blockers and taste enhancers making the dosage form palatable.

Suitable sweeteners include aspartam, saccharine, sodium saccharinate, potassium acesulfam, maltitol, isomaltidex, sodium cyclamate and sucralose. Preferred sweeteners are aspartam, acesulfam, acesulfam potassium and sucralose.

Preferably, the sweetener or mixture thereof is present in an amount of about 0.5% to about 25%, more preferably of about 0.5% to about 15% by weight with respect to the unit dose weight.

In further preferred embodiments, the oral lyophilizate of modafinil comprises flavors including notably one or more aromatic oils, natural or synthetic aromatics oils fixed on a powder support. Aromatic oils include, among others, peppermint, tutti frutti, pineapple, cherry, strawberry, banana, bubble gum, grape, raspberry and blackcurrant.

Preferably, the flavors are present in an amount of about 1% to about 10% by weight with respect to the unit dose weight.

As a complement, bitter blockers may be added to the composition up to about 15% by weight with respect to the unit dose weight. Notably are used: bitter blocker and bitter mask.

Appropriate taste enhancers include notably citric acid. A quantity of up to about 5% by weight with respect to the unit dose weight is generally sufficient.

2.c) Other Excipients

Diluents are used to dilute the active ingredient and confer body to the dosage form. Suitable diluents include dicalcium phosphate dihydrate, calcium sulphate, lactose, cellulose and cellulose derivatives, cyclodextrin and cyclodextrin derivatives, kaolin, mannitol, sodium chloride, dry starch, hydrolyse starches, silicon dioxide, titanium oxide, alumina, talc, isomaltidex, microcrystalline cellulose and powdered sugar and mixtures thereof. Particularly preferred are lactose, mannitol, isomaltidex and mixture thereof.

The oral lyophilizate may include diluents up to about 80% by weight of the unit dose weight. Preferably, the compositions include up to about 50% of diluents and more preferably up to about 25% and most preferably up to about 5% of diluent by weight with respect to the unit dose weight.

Binders may be used to impart cohesive qualities to the oral lyophilizate. Suitable binders include, but are not limited to, starch, gelatine, sugars (including sucrose, glucose, dextrose, lactose and sorbitol), polyethylene glycol, waxes, natural and synthetic gums, acacia, adragante, sodium alginate, cellulose, cellulose derivatives and veegum, and synthetic polymers such as polymethacrylate and polyvinylpyrrolidone and mixtures thereof. Dextran, polyvinylpyrrolidone, methyl cellulose and hydroxypropylmethyl cellulose are particularly preferred.

Preferably, the binder is present in an amount of up to about 5% by weight with respect to the unit dose weight.

Suspension agents may be useful for the preparation of the suspension containing modafinil and the other excipients. Appropriate suspension agents include notably methylcellulose.

Surfactants may be anionic, cationic, amphoteric and non-ionic agents, with anionic surfactants preferred. Suitable anionic surfactants include, but are not limited to, those containing carboxylate, sulfonate and sulphate ions, associated with cations such as sodium, potassium and ammonium ions. Particularly preferred surfactants include sucroesters 7, 11 or 15, polysorbate 20, 60, 80, poloxamers 188, 407, TEF 300, 400, sorbitan stearate and mixtures thereof.

Preferably, the surfactant is present in an amount of about 0.1% to about 5% by weight with respect to the unit weight of the lyophilizate.

Suitable disintegrants include copovidone and cross-povidone. They are added in an appropriate quantity to ensure a disintegration of the oral lyophilizate. Generally, a quantity of up to about 5% by weight of disintegrant with respect to the unit dose weight is sufficient.

Secondary excipients may also be included in the oral lyophilizate, such as for example buffers or acids and bases to adjust the pH, salts, preservatives, notably bactericides, viscosity enhancers, antioxidants or chelating agents.

Useful buffers include carbonate, borate, phosphate, citrate, tri(hydroxyl-methyl)aminomethane, maleate and tartrate buffers.

Examples of preservatives include methyl or propyl parahydroxy-benzoate, benzethonium chloride, benzyl alcohol, butylated hydroxyl anisol (BHA), sorbic acid, sodium benzoate.

It is noted that some excipients may have additional properties that must be taken into account when developing a Lyoc™ formulation. As examples, diluents may also function as disintegrants and binders, and binders (such as methylcellulose) may also function as suspension agents and surfactants.

In a preferred embodiment, the oral lyophilizate comprises modafinil particles with a median diameter between 10 and 200 µm, preferably between 20 and 40 µm.

In that embodiment, the use of an excipient with strong taste-masking power is preferred in order to avoid the manufacture of bulky lyophilizates. A more preferred composition comprises modafinil particles coated with fatty acid glycerol ester. These coated modafinil particles may be present in the composition in admixture with cyclic oligosaccharides, in particular cyclodextrin, if necessary.

In another preferred embodiment, the oral lyophilizate comprises modafinil particles with a median particle size diameter between 200 and about µm.

In a preferred embodiment, the oral lyophilizate may be administered directly by oral route, but it can also be used to constitute a suspension in water prior to the administration by oral route.

Manufacture

In another aspect, the present invention provides a method for the manufacture of an oral lyophilizate according to the invention comprising:
(i) preparing a water suspension comprising modafinil particles having a median diameter of about 10 to about 1000 µm, at least one excipient selected from the group consisting of cyclic oligosaccharides, fatty acid esters of glycerol, sweeteners or a mixture thereof and optionally one or more excipients;
(ii) lyophilizing the resulting suspension to obtain the oral lyophilizate.

Preferably, the preparation of the suspension of step (i) comprises the following steps:
a) preparing a mixture from modafinil particles having a median diameter of about 10 to about 1000 µm, at least one excipient selected from the group consisting of cyclic oligosaccharides, fatty acid esters of glycerol, sweeteners or a mixture thereof, and optionally one or more excipients;
b) granulating the resulting mixture; and
c) suspending the obtained granules in water.

The quantity of water employed in step c) is carefully monitored in order to obtain a homogeneous suspension with an adequate viscosity critical. However, this quantity is preferably limited to the amount necessary for producing the suspension of step c) in view of the following lyophilization.

According to one preferred embodiment, the modafinil particles used in step a) are coated by the fatty acid ester glycerol prior to the mixing with the excipient.

The coated modafinil particles may be obtained by the following steps:
a1) heating the modafinil particles at a temperature between 30° to 50° C.;
a2) mixing the modafinil particles with a melted fatty acid ester of glycerol;
a3) mixing the resulting coated modafinil particles with at least one excipient selected from the group consisting of cyclic oligosaccharides, fatty acid esters of glycerol, sweeteners or a mixture thereof, and optionally one or more excipients.

The liquid mixture resulting from step (i) may be distributed into alveolar packs before lyophilization.

For detailed information concerning materials, equipments and processes for the manufacture of oral lyophilizates, reference is made to Remington's Pharmaceutical Sciences, 1990, 18$^{th}$ Edition, MACK Publishing Company Ed.

Typically, the lyophilization of the suspensions is done as follows:

The suspensions are subjected to a cycle of freezing, then of sublimation under a reduced pressure suitable for the volume to be lyophilized.

Preferably, the lyophilization is performed with a freezing rate of −1°/min to −2° C./min in a freeze-drier of type Usifroid SMH200 or 600 (Usifroid, France).

The time, pressure and temperature of the sublimation phase are adjusted according to the volume of the mixture to be lyophilized and to the desired residual water content in the lyophilizate.

The lyophilizate may then be shelved at 25° C. or even up to 65° C. without altering the chemical stability of the modafinil.

All the materials used in the following examples are commercially available or can be readily prepared by one skilled in the art by known methods.

Another aspect of the invention also includes the use of lyophilizates for the treatment of a disease or disorders in a subject in need thereof comprising administering to the subject a therapeutically effective amount of the compositions of the present invention. In particular, the present compositions are useful for the treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder and fatigue, shift work sleep disorders, depression and improvement of cognitive dysfunction.

EXAMPLES

Material and Methods

The modafinil particles of size 20-40 μm are commercially available (Cephalon, Inc., West Chester, Pa.). The modafinil particles of size 1-10 μm were prepared by micronizing modafinil particles of commercial grade 20-40 μm using a micronizer type Jet mill (Microjet Mill, Switzerland). The modafinil particles of size 200-315 μm were obtained by screening an API modafinil batch (Active Pharmaceutical Ingredient) through a 200 μm screen and a 315 μm screen. Modafinil lot with bounded particles size may be prepared by methods discloses in WO 2004/006905.

The glycerol palmitostearate was purchased as Precirol ATO 5® from Gattefossé (France).

Measurement of the Dissolution Kinetics of Oral Lyophilizates (Dissolution Assay)

The modafinil dissolution rate of oral lyophilizates was measured according to the following protocol.

The solutions to be analyzed were prepared by introducing an oral lyophilizate into 1 L of HCl 0.1 M kept at a temperature of 37° C.±0.5° C. under stirring at 100 rpm. Samples were taken at 5, 15, 30, 60, 120 and 180 min and analyzed by HPLC runs under the following conditions:

Column: ODS, 3, 3.5 μm, 7.5 cm×4.6 mm
Column temperature: 40° C.
Mobile phase: Acetonitrile/water (50/50 v)
Flow rate: 1.0 ml/min
Detection: UV=220 nm
Injection volume: 5 μL The percentage of modafinil dissolved was calculated by comparison with a run obtained under the same conditions from a standard modafinil solution.

Figure 1:
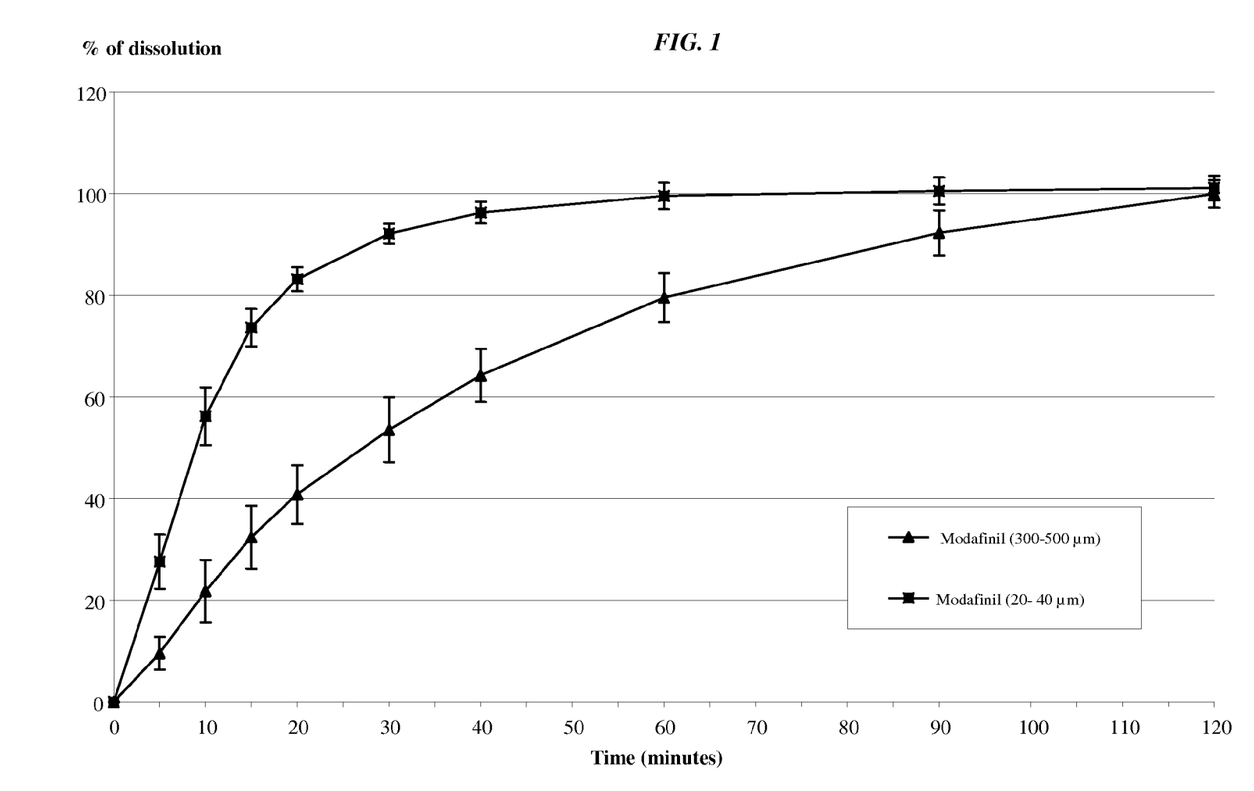
FIG. 1: shows the dissolution kinetics in 0.1M HCl at 37° C. of oral lyophilizates comprising modafinil with particle size of 20-40 µm as compared to particle size of 300 to 500 µm.
Figure 2:
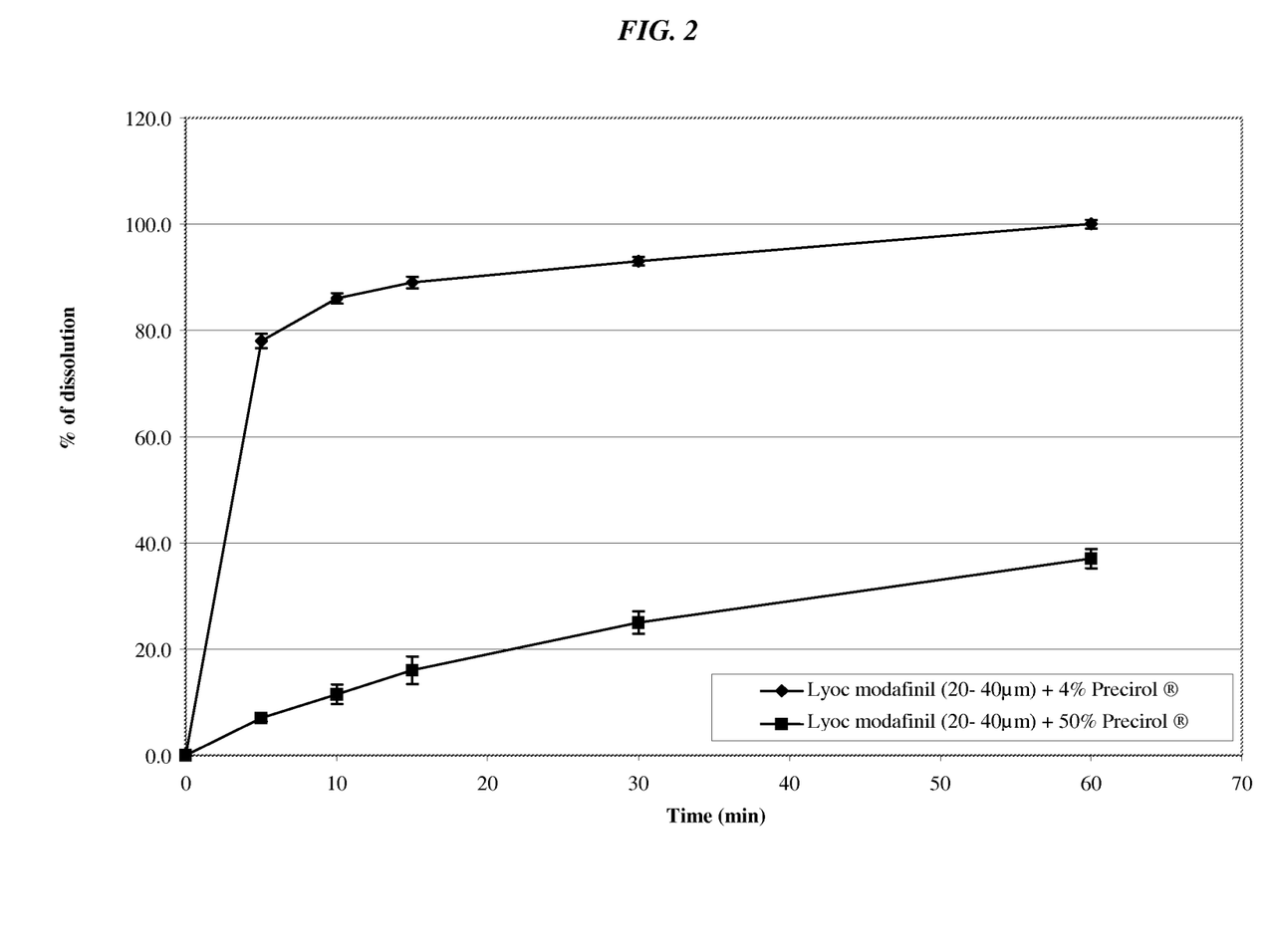
FIG. 2: shows the dissolution kinetics in 0.1M HCl at 37° C. of oral lyophilizates comprising modafinil particles coated with either 4% or 50% of Precirol® ATO5.
Figure 3:
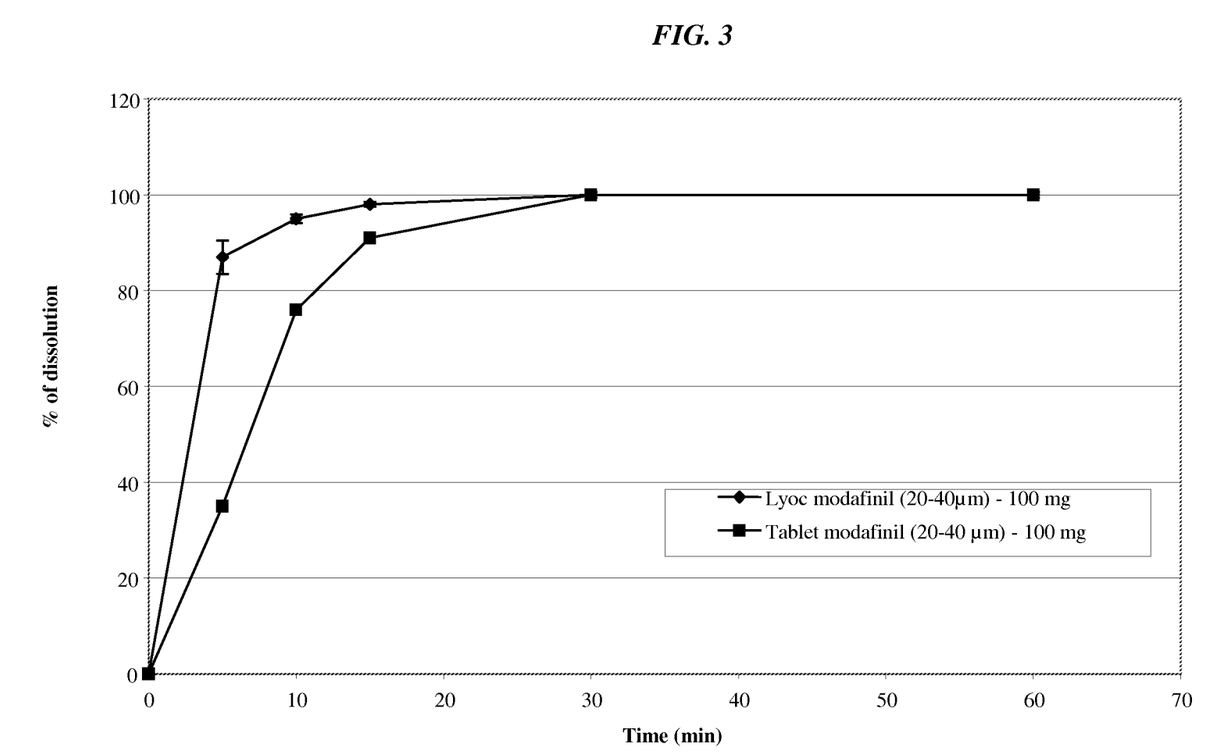
FIG. 3: shows the dissolution kinetics in 0.1M HCl at 37° C. of oral lyophilizates in comparison with a commercial modafinil tablet (particle size: 20-40 µm).

The dissolution at 30 minutes of different formulations is reported in the following tables. The dissolution kinetics obtained with different particle sizes are shown in FIGS. 1 to 3.

The conductivity analysis was performed by differential thermal analysis with a Lyotherm apparatus (DTA equipment, Biopharma Ltd, UK). The lyophilization was performed with a SMH 50 apparatus (Usifroid, France).

Measurement of Disintegration Time

Two methods may be used:
  the method recommended by Pharmeuropa: one dose unit of oral lyophilizate is introduced in a beaker containing 200 ml of water at 15° C.-20° C. The time for total disintegration is measured. The measurement is repeated in five separate experiments. Results are given as a mean value (n=5) and expressed in seconds.
  the method according to USP <701> (US Pharmacopoeia). Results are given as a mean (n=6) and expressed in seconds.

Measurement of Hardness (According to the European Pharmacopoeia)

The measurement of hardness was performed with the Schleuniger® apparatus (Schleuniger, France). It is an electrical test equipment which eliminates operator variability. The force required to break a tablet or a lyophilizate unit (Lyoc®) is expressed in Newton. The test is repeated on 5 separate occasions on 5 individual unit doses. Results are given as a mean value and expressed in Newton.

Measurement of Residual Humidity

Loss on drying is determined by thermogravimetric analysis using a sensitive electrobalance according to USP <731>.

General Process for Oral Lyophillizates Preparation

In a suitable blender, the modafinil particles were mixed with lactose and/or mannitol, aspartam, acesulfam, sucralose, citric acid, flavor, bitter blocker, betacyclodextrin as powder. The respective quantities of the above mentioned ingredients are shown in the tables corresponding to the different examples.

A solution composed of sucroester, dextran 70, isomalt and water (or isomalt, dextran 70, methyl cellulose and water; or isomalt, methyl cellulose, glycerylpalmitostearate and water) was added to the blender and mixed until a stable suspension was obtained.

A conductivity analysis was performed in order to determine the freezing or eutectic point=−32° C.

The mixture was dispensed into PVC blisters with round cavities and cooled between the shelves of a lyophilizer (Usifroid SMH 50 or SMH 100 or SMH 600 depending on batch size; Usifroid, France). After freezing below a temperature of −35° C. over a period of at least 30 minutes, the mixture was subjected to lyophilization at a pressure of 350-400 microbars during at least 3 hours. The temperature of the mixture increased from −35° C. to +40° C./45° C.

A secondary drying was performed at a pressure of 50 microbars at 45° C. during at least 30 minutes.

The product obtained had a uniform tronconic shape with a maximum diameter (or upper diameter) comprised between 10 to 20 mm and a thickness between 2 mm and 10 mm, a porous state and a unitary weight. The blisters were then heat-sealed with sheets of aluminum and packaged.

Examples 1 to 4

TABLE I

| | Examples | | | |
|---|---|---|---|---|
| | 1 | 2 | 3 | 4 |
| | Modafinil particle size | | | |
| | 1-10 μm | 20-40 μm | 200-315 μm | 300-500 μm |
| Modafinil | 280 mg | 280 mg | 300 mg | 300 mg |
| Copovidone | 0.7 mg | 0.7 mg | 0.7 mg | 0.7 mg |
| Dextran 70 | 15 mg | 15 mg | 15 mg | 15 mg |
| Aspartam | 7 mg | 7 mg | 7 mg | 7 mg |
| Acesulfam K | 10 mg | 10 mg | 10 mg | 10 mg |
| Flavor (pineapple) | 15 mg | 15 mg | 15 mg | 15 mg |
| Citric acid | 5 mg | 5 mg | 5 mg | 5 mg |
| Mannitol | 367.3 mg | 367.3 mg | 347.3 mg | 347.3 mg |
| Water | 380 mg | 380 mg | 380 mg | 380 mg |
| Unit weight | 700 mg | 700 mg | 700 mg | 700 mg |
| Taste | Bitter | Bitter | Masked | Masked |
| Dissolution at 30 mn | 100% | 96% | 85% | 53% |

As apparent from Table I, oral lyophilizates of modafinil with small particle size (1-10 μm or 20-40 μm) exhibited a bitter taste while an equivalent formulation prepared with large particle size (superior to 200 μm) is have a masked taste. However, the dissolution of oral lyophilizates with large particles is notably slower (FIG. 1).

Examples 5 and 6

Oral lyophilizates were prepared as Example 1 according to the formulations set out in Table II and using modafinil particles of 20-40 μm coated with 4% and 50% by weight of glycerylpalmitostearate with respect to modafinil weight, respectively.

These coated modafinil particles were prepared by melting a specified quantity of glycerylpalmitostearate (Precirol® ATO5 from Gattefossé) in an appropriate vessel (a planetary or a turbosphere mixer) at about 60° C.-65° C. Modafinil of the specified particle size was then introduced and mixed until homogeneization. The obtained granules were screened through a 1 mm screen and stored at room temperature. They are used according to the same procedure as uncoated particles.

TABLE II

| | Examples | |
|---|---|---|
| | 5<br>Modafinil (96%)<br>Precirol ® ATO 5 (4%) | 6<br>Modafinil (50%)<br>Precirol ® ATO 5 (50%) |
| Modafinil (20-40 μm) | 300 mg | 140 mg |
| Precirol ® ATO 5 | 12.5 mg | 140 mg |
| Copovidone | 0.7 mg | 0.7 mg |
| Dextran 70 | 15 mg | 15 mg |
| Aspartam | 7 mg | 7 mg |
| Acesulfam K | 10 mg | 10 mg |
| Flavor (pineapple) | 15 mg | 15 mg |
| Citric acid | 5 mg | 5 mg |
| Mannitol | 344.8 mg | 377.3 mg |
| Water | 390 mg | 390 mg |
| Unit weight | 700 mg | 700 mg |
| Taste | Masked | Masked |
| Dissolution test | 93% at 30 mn | 25% at 30 mn<br>57% at 180 mn |

The obtained oral lyophilizates are taste-masked.

Moreover, it is noted that while the formulation of example 5 with a glycerylpalmitostearate modafinil weight ratio of 0.04 presents a dissolution rate similar to lyophilizate prepared with uncoated modafinil particles. The dissolution profile of the lyophilizate of example 6 with a glycerylpalmitostearate/modafinil weight ratio of 1 shows sustained-release properties (FIG. 2).

Examples 7 to 16

Examples 8 to 16 correspond to various oral lyophilizates of modafinil with taste-masked properties, prepared according to Example 1 according to the formulations given in Table III with different dosages of modafinil, under the form of particles of 20-40 μm.

The lyophilizates prepared were also characterized in terms of mechanical strength as set out above. The dissolution profile of lyophilizates (20-40 μm) [example 11] was similar to those of tablets (20-40 μm) (FIG. 3).

TABLE III

| Examples | 7 | 8 | 9 | 10 |
|---|---|---|---|---|
| Modafinil (20-40 μm) | 85 mg | 85 mg | 85 mg | 170 mg |
| Copovidone | 0.7 mg | 0.7 mg | 0.7 mg | 1 mg |
| Dextran 70 | 15 mg | 15 mg | 15 mg | 20 mg |
| Aspartam | 7 mg | 7 mg | 7 mg | 5 mg |
| Acesulfam K | 10 mg | 10 mg | 10 mg | 8 mg |
| Flavor (pineapple or cherry, strawberry...) | 15 mg | 15 mg | 15 mg | 15 mg |
| Citric acid | 2 mg | 2 mg | 2 mg | 2 mg |
| Bitter blocker | — | — | — | 2 mg |
| β cyclodextrin | — | 150 mg | 200 mg | 200 mg |
| Mannitol | 470.5 mg | 320.5 mg | 270.5 mg | 277 mg |
| Water | 350 mg | 300 mg | 300 mg | 350 mg |
| Unit weight | 600 mg | 600 mg | 600 mg | 700 mg |
| Taste | Bitter | Masked | Masked | Masked |
| Disintegration time | 30 sec | 30 sec | 40 sec | 40-60 sec |

| Examples | 11 | 12 | 13 |
|---|---|---|---|
| Modafinil (20-40 μm) | 100 mg | 100 mg | 300 mg |
| Povidone K 30 | — | 5 mg | — |
| Dextran 70 | 5 mg | — | 15 mg |
| Aspartam | 9 mg | 9 mg | 9 mg |
| Acesulfam K | 1 mg | 1 mg | 1 mg |
| Flavor pineapple | 15 mg | — | 15 mg |
| Tutti frutti | — | 10 mg | — |
| Citric acid | 10 mg | 10 mg | 10 mg |
| β cyclodextrin | 150 mg | 150 mg | 300 mg |
| Mannitol | 310 mg | 310 mg | 145 mg |
| Water | 350 mg | 350 mg | 350 mg |
| Unit weight | 600 mg | 595 mg | 795 mg |
| Taste | Masked | Masked | Masked |
| Disintegration time | 10-15 sec | 10-15 sec | 20-40 sec |
| Hardness | 10-15N | 8-10N | 20-35N |

| Examples | 14 | 15 | 16 |
|---|---|---|---|
| Modafinil (20-40 μm) | 200 mg | 200 mg | 200 mg |
| Povidone K 30 | 10 mg | 10 mg | — |
| Dextran 70 | — | — | 5 mg |
| Aspartam | 10 mg | 10 mg | 5 mg |
| Acesulfam K | 1 mg | 1 mg | 10 mg |
| Flavor pineapple | 15 mg | — | 15 mg |
| Tutti frutti | — | 10 mg | — |
| Mint liquorice | — | — | — |
| Citric acid | 10 mg | 10 mg | 5 mg |
| β-cyclodextrin | 200 mg | 200 mg | 200 mg |
| Mannitol | 254 mg | 259 mg | 260 mg |
| Water | 350 mg | 350 mg | 350 mg |
| Unit weight | 700 mg | 700 mg | 700 mg |
| Taste | Masked | Masked | Masked |
| Disintegration time | 40-50 sec | 30-50 sec | 20-30 sec |
| Hardness | 15-20N | 20-25N | 30-40N |

Comparison of examples 8 to 16 with example 7 comprising the same quantity of sweeteners and flavors shows that an oral lyophilizate with a cyclodextrin:modafinil molar ratio lower than 0.6:1 is efficiently taste-masked. The addition of a bitter blocker (example 10) to the formulation allowed the further decrease of the quantity of cyclodextrin added to a molar ratio of less than 0.3.

Examples 17 to 27

Oral lyophilizates of modafinil were prepared according to Example 5 using the formulations given in Table IV with different dosages of modafinil, under the form of particles of 20-40 μm coated with glycerylpalmitostearate (Precirol® ATO5). The formulations included also a low quantity of cyclodextrin with a cyclodextrin:modafinil molar ratio in the 0.14:1 to 0.05:1 range. The total quantity of glycerolpalmitostearate and of cyclodextrin are sufficient to taste-mask modafinil bitter taste. Unit dose weights are appropriately below 800 mg (in the 800 mg-126 mg range depending on the modafinil weight percent) and contain a high weight percent of modafinil per unit dose (Formulations 21 to 27 included about 67% of modafinil).

The lyophilizates prepared were also characterized in terms of mechanical strength.

TABLE IV

| Examples | 17 | 18 |
|---|---|---|
| Modafinil (20-40 μm) | 255 mg | 255 mg |
| Precirol ® ATO 5 | 6 mg | 6 mg |
| Isomaltidex | 24 mg | 12 mg |
| Dextran 70 | 3 mg | 9 mg |
| Citric acid | 3 mg | — |
| Sucroester 11 | — | 1 mg |
| Aspartam | 9 mg | 9 mg |
| Acesulfam potassium | 9 mg | 9 mg |
| Flavor (raspberry) | 12 mg | 18 mg |

TABLE IV-continued

| | | |
|---|---|---|
| Beta-cyclodextrin | 60 mg | 60 mg |
| Lactose QSP 480 | 99 mg | 101 mg |
| Purified water | 240 mg | 240 mg |
| Unit weight | 480 mg | 480 mg |
| Taste | Masked | Masked |
| Disintegration time | 40-60 sec | 40-60 sec |
| Hardness | 20-40N | 30-40N |

| Examples | 19 | 20 |
|---|---|---|
| Modafinil (20-40 µm) | 425 mg | 425 mg |
| Precirol ® ATO 5 | 10 mg | 10 mg |
| Isomaltidex | 20 mg | 20 mg |
| Dextran 70 | 15 mg | 15 mg |
| Sucroester 11 | 2 mg | 5 mg |
| Aspartam | 15 mg | 15 mg |
| Acesulfam potassium | 15 mg | 15 mg |
| Flavor (tutti frutti) | 30 mg | 30 mg |
| Betacyclodextrin | 80 mg | 80 mg |
| Lactose QSP 800 mg | 188 mg | — |
| Mannitol QSP 800 mg | — | 185 mg |
| Purified water | 400 mg | 400 mg |
| Unit Weight | 800 mg | 800 mg |
| Taste | Masked | Masked |
| Disintegration time | 40-60 sec | 30-50 sec |
| Hardness | 30-50N | 25-40N |

| Examples | 21 | 22 |
|---|---|---|
| Modafinil (20-40 µm) | 425 mg | 425 mg |
| Precirol ® ATO 5 | 10 mg | 10 mg |
| Isomaltidex | 20 mg | 20 mg |
| Methylcellulose | 5 mg | — |
| Hydroxymethyl cellulose | — | 10 mg |
| Aspartam | 20 mg | 17 mg |
| Acesulfam potassium | 20 mg | 17 mg |
| Flavor (strawberry or pinapple) | 30 mg | 30 mg |
| Betacyclodextrin | 100 mg | 101 mg |
| Purified water | QS | QS |
| Unit Weight | 630 mg | 630 mg |
| Taste | Masked | Masked |
| Disintegration time | 10-20 sec | 20-30 sec |
| Hardness | 10-20N | 15-30N |

Unit doses comprising 85 mg, 170 mg, 255 mg and 340 mg of modafinil were prepared accordingly, so as to maintain the relative proportions of other pharmaceutical composition ingredients as compared to examples 21 to 22. The final weight of lyophilizates was 126 mg, 252 mg, 378 mg and 504 mg, respectively and the taste of modafinil was masked and the measurement of disintegration time and hardness were within the same ranges.

| Examples | 23 | 24 |
|---|---|---|
| Modafinil (20-40 µm) | 425 | 255 |
| Precirol ® ATO 5 | 10 | 6 |
| Isomaltidex | 20 | 12 |
| Methylcellulose | 5 | 5 |
| Aspartam | 20 | 12 |
| Acesulfam potassium | 20 | 12 |
| Flavor (strawberry) | 30 | 18 |
| cyclodextrin | 100 | 60 |
| Purified water | 530 | 378 |
| Unit weight | 630 | 380 |
| Taste | Masked | Masked |
| Disintegration time | 3 sec | 3 sec |
| Hardness | 7N | 7N |

| Examples | 25 | 26 | 27 |
|---|---|---|---|
| Modafinil (20-40 µm) | 425 | 340 | 255 |
| Precirol ® ATO 5 | 10 | 8 | 6 |
| Isomaltidex | 20 | 16 | 12 |
| Methylcellulose | 2 | 1.6 | 1.2 |
| Aspartam | 20 | 16 | 12 |
| Acesulfam potassium | 20 | 16 | 12 |
| Flavor (Cherry) | 15 | 12 | 9 |
| Beta-cyclodextrin | 118 | 94.4 | 70.8 |
| Purified water | 500 | 400 | 300 |
| Unit weight | 630 | 504 | 378 |
| Taste | Masked | Masked | Masked |
| Disintegration time | 3 sec | 3 sec | 3 sec |
| Hardness | 8.3N | 8N | 7N |

Examples 28 to 33

Oral lyophilizates of modafinil were prepared according to Example 5 using the formulations given in Table V with different dosages of modafinil, under the form of coated particles of 20-40 µm. The formulations include Precirol® ATO5 as taste-masking agent. The lyophilizates prepared were also characterized in terms of mechanical strength.

TABLE V

| Examples | 28 | 29 | 30 |
|---|---|---|---|
| Modafinil (20-40 µm) | 255 mg | 340 mg | 425 mg |
| Precirol ® ATO 5 | 3 mg | 4 mg | 5 mg |
| Isomaltidex | 6 mg | 8 mg | 10 mg |
| Aspartam | 12 mg | 16 mg | 20 mg |
| Acesulfam potassium | 9 mg | 12 mg | 15 mg |
| Flavor (strawberry) | 18 mg | 24.6 mg | 30 mg |
| Methyl cellulose | 1.80 mg | 2.40 mg | 3 mg |
| Purified water | 258 mg | 344 mg | 430 mg |
| Unit Weight | 304.8 mg | 406 mg | 508 mg |
| Taste | Masked | Masked | Masked |
| Disintegration time | 10 sec | 12 sec | 15 sec |
| Hardness | 9.5N | 9.5N | 9N |

| Examples | 31 | 32 | 33 |
|---|---|---|---|
| Modafinil (20-40 µm) | 425 | 340 | 255 |
| Precirol ATO 5 | 5 | 4 | 3 |
| Isomaltidex | 10 | 8 | 6 |
| Methylcellulose | 3 | 2.4 | 1.8 |
| Aspartam | 20 | 16 | 12 |
| Acesulfam potassium | 20 | 16 | 12 |
| Flavor (grape, strawberry . . .) | 30 | 24 | 18 |
| Purified water | 430 | 378 | 378 |
| Unit weight | 513 | 410 | 308 |
| Taste | Masked | Masked | Masked |
| Disintegration time | 15 sec | 10 sec | 5 sec |
| Hardness | 17N | 17N | 16N |

It may be concluded that the formulation of an oral lyophilizate using a proportion of modafinil particles coated with fatty acid glycerol esters and/or cyclic oligosaccharides allows a taste masking of high dosages of modafinil without exceeding a limited total weight. The oral dosage form of modafinil is suitable for the administration of high dosages in one unit, is easily swallable and has an acceptable taste.

Examples 34(a,b) to 38

Oral lyophilizates 34(a,b) to 38 were prepared as the General Procedure of Example 1, according to the formulations set out in table VI.

TABLE VI

| Examples | 34a | 34b | 35a | 35b | 35c |
|---|---|---|---|---|---|
| Modafinil (20-40 µm) | 425 | 340 | 255 | 170 | 85 |
| Glyceryl ester | 5 | 4 | 3 | 2 | 1 |

TABLE VI-continued

|  |  |  |  |  |  |
|---|---|---|---|---|---|
| Methyl cellulose | 3 | 2.4 | 2.4 | 1.2 | 0.6 |
| Sucralose | 30 | 24 | 20 | 12 | 6 |
| Flavor (grape, strawberry, bubble gum) | 30 | 24 | 20 | 12 | 6 |
| Lactose | — | — | 83 | 55.3 | 27.7 |
| Purified water | 450 mg | 360 mg | 360 mg | 240 mg | 120 mg |
| Unit weight after lyophilization | 493 mg | 394 mg | 383 mg | 255 mg | 127.6 mg |
| Taste masking | Masked | Masked | Masked | Masked | Masked |
| Disintegration | 20 sec | 15 sec | 10 sec | 5 sec | 5 sec |
| Drug loading | 86.2% | 86.2% | 66.6% | 66.6% | 66.6% |
| In vitro dissolution at 15 min | >90% | >90% | >90% | >90% | >90% |
| Size of lyoc (d × h) mm | 15 × 6 | 15 × 5 | 14.5 × 5 | 14.5 × 4 | 13 × 2 |

| Examples | 36 | 37 |
|---|---|---|
| Modafinil (100-315 μm) | 425 | 255 |
| Methyl cellulose | 3 | 2.4 |
| Sucralose | 30 | 20 |
| Flavor (grape, bubble gum, fruit punch) | 30 | 24 |
| Lactose | — | 77 |
| Purified water | 450 mg | 380 mg |
| Unit weight with water | 938 | 780 |
| Unit weight after lyophilization | 488 | 400 |
| Taste masking | Masked | Masked |
| Drug loading | 87% | 63.75% |
| Disintegration time | 30 sec | 10 sec |
| In vitro dissolution at 15 min | >80% | >80% |
| Size of lyoc (d × h) mm | 15 × 6 | 14.5 × 5 |

| Examples | 38 |
|---|---|
| Modafinil (100-315 μm) | 425 |
| Sucralose | 30 |
| Dextran 70 | 30 |
| Xanthan gum | 1 |
| Flavor (fruit punch) | 20 |
| Lactose | 94 |
| Purified water | 700 mg |
| Unit weight after lyophilization | 600 mg |
| Taste masking | Masked |
| Drug loading | 70.8% |
| Disintegration time | 15 seconds |
| In vitro dissolution at 15 min | >80% |
| Size of lyoc (d × h) mm | 16.5 × 7 |

Examples 34 (a,b) to 38 show examples of modafinil lyophilizates, prepared with a limited number of excipients (3 to 5), a very high modafinil loading: from 67 to 86%, which advantageously may be prepared to cover a with range of Modafinil dose. These small size lyophilizates of modafinil have bitter taste masked properties and disintegrate extremely rapidly within 5 to 20 second range.

Although the present invention has been described in considerable detail, those skilled in the art will appreciate that numerous changes and modifications may be made to the embodiments and preferred embodiments of the invention and that such changes and modifications are within the scope of the present invention. Additionally, each reference cited hereby is incorporated by reference.

The invention claimed is:

1. A method for the manufacture of an oral lyophilizate comprising taste masked modafinil particles, comprising the steps of:
   (i) coating modafinil particles having a median diameter of less than 200 μm with a fatty acid ester of glycerol to provide taste masked modafinil particles;
   (ii) preparing a water suspension comprising the taste masked modafinil particles; and
   (iii) lyophilizing the suspension;
   wherein when the oral lyophilizate is introduced into 1 L of 0.1M HCl at 37° C. more than 75% by weight of the modafinil dissolves in 30 minutes.

2. The method according to claim 1, wherein the fatty acid ester of glycerol is chosen from fatty acid monoglycerides, fatty acid diglycerides, fatty acid triglycerides, and mixtures thereof.

3. The method according to claim 2, wherein the fatty acid ester of glycerol is derived from dibehenic acid, palmitostearic acid, stearic acid, oleic acid, linoleic acid, caprylic acid, capric acid, or mixtures thereof.

4. The method according to claim 1, wherein the modafinil is the levorotatory isomer of modafinil.

5. The method according to claim 1, wherein the modafinil is the dextrorotatory isomer of modafinil.

6. The method according to claim 1, wherein when the oral lyophilizate is introduced into 1 L of 0.1 M HCl at 37° C. more than 85% by weight of the modafinil dissolves in 30 minutes.

7. The method according to claim 1, wherein the modafinil particles have a median diameter of between 20 and 40 μm.

8. The method according to claim 1, wherein the oral lyophilizate comprises about 50 mg to about 850 mg of modafinil.

9. The method according to claim 1, wherein when the oral lyophilizate is introduced into 1 L of 0.1 M HCl at 37° C. more than 80% by weight of the modafinil dissolves in 10 minutes.

10. The method according to claim 1, wherein when the oral lyophilizate is introduced into 1 L of 0.1 M HCl at 37° C. more than 90% by weight of the modafinil dissolves in 15 minutes.

11. The method according to claim 1, wherein the oral lyophilizate has a disintegration time of less than 3 minutes, as measured according to the USP method (<701> USP 26).

12. The method according to claim 1, wherein the oral lyophilizate has a disintegration time of 2 to 60 seconds, as measured according to the USP method (<701> USP 26).

13. The method according to claim 1, wherein the oral lyophilizate has a hardness of 5 N to 60 N as measured with the Schleuniger® apparatus (Schleuniger, Switzerland).

14. The method according to claim 1, wherein the oral lyophilizate has a hardness of 7 N to 30 N as measured with the Schleuniger® apparatus (Schleuniger, Switzerland).

* * * * *